United States Patent [19]

Sadeh

[11] Patent Number: 4,732,158

[45] Date of Patent: Mar. 22, 1988

[54] METHOD AND APPARATUS FOR MONITORING ELECTROCARDIOGRAM (ECG) SIGNALS

[75] Inventor: Dror Sadeh, Ramat Hasharon, Israel

[73] Assignee: Ramot University Authority for Applied Research & Industrial Development Ltd., Tel Aviv, Israel

[21] Appl. No.: 316,065

[22] Filed: Oct. 28, 1981

[30] Foreign Application Priority Data

Nov. 12, 1980 [IL] Israel ........................................ 61465

[51] Int. Cl.$^4$ .............................................. A61B 5/04
[52] U.S. Cl. ........................................ 128/702; 364/417
[58] Field of Search ...................... 128/696, 702, 704; 364/415, 417

[56] References Cited

U.S. PATENT DOCUMENTS

| | | | |
|---|---|---|---|
| 3,654,916 | 4/1972 | Nielson | 128/702 |
| 4,121,576 | 10/1978 | Greensite | 128/699 |
| 4,170,992 | 10/1979 | Dillman | 128/702 |
| 4,279,258 | 7/1981 | John | 128/731 |

OTHER PUBLICATIONS

Wajszczuk et al, "Circulation", vol. 58, No. 1, Jul. 1978, pp. 95–102.
Wallingford et al, "I.E.E.E. Transactions on Instrumentation and Measurement", vol. 27, No. 1, Mar. 1978, pp. 70–73.

Primary Examiner—William E. Kamm
Attorney, Agent, or Firm—Benjamin J. Barish

[57] ABSTRACT

A method and apparatus for monitoring ECG signals are described characterized in that an ECG signal wave is detected, filtered to pass only a frequency band within a range of about 25–300 Hz, and stored in a first storage device; and each successive ECG signal wave is then detected, similarly filtered, and stored in a second storage device. Each of the successive signal waves, when stored in the second storage device, is cross-correlated with the signal wave stored in the first storage device, and a determination is made whether the maximum cross-correlation coefficient exceeds a predetermined value. Each of the successive signal waves having a maximum cross-correlation coefficient exceeding the predetermined value is averaged with the waves stored in the first storage device following which it is stored in the first storage device in place of the signal wave previously stored therein, and is also displayed.

15 Claims, 3 Drawing Figures

METHOD AND APPARATUS FOR MONITORING ELECTROCARDIOGRAM (ECG) SIGNALS

BACKGROUND OF THE INVENTION

The present invention relates to a method and apparatus for monitoring electrocardiogram (ECG) signals as an aid in studying and diagnosing abnormal heart activity.

ECG signals are electrical potential traces or waves accompanied by the contraction of the different cavities of the heart. They are an important aid in the study and diagnosis of abnormal heart activity. A typical ECG signal, produced by placing electrodes against the patient's skin, includes P, Q, R, S and T waves, which are all easily discernable by existing equipment. Thus, these ECG signals are commonly measured by a pen on paper at frequencies of 0–50 Hz, this frequency range being normally sufficient for discerning the above waves since the heartbeat rate is approximately 1 second, and the rise time of these waves is in the order of 0.1 second.

BRIEF SUMMARY OF THE INVENTION

The present invention is based on the physiological discovery that patients suffering from an infarct condition, and certain other heart disorders, show very small but fast changes in their ECG signal waves. If the infarct or the damage in the heart muscle is extensive, it can be seen in the usual ECG monitored by existing equipment; but if the infarct is small, it causes a minute change in the flow of electricity in the heart, producing a fast and small pulse which would not otherwise be detected by the ECG monitoring equipment.

The present invention provides a novel method and apparatus for monitoring ECG signals in order to detect these smaller-amplitude, higher-frequency waves which may indicate a small infarct or another heart disorder.

Briefly, the small, fast changes in the ECG signal waves are detected by first filtering the ECG signal via a relatively high-frequency band-pass filter in order to remove low-frequency components, namely the P, Q, R, S and T waves, and then cross-correlating successive ones of the filtered waves. The cross-correlation is performed in order to determine the exact phase of each ECG signal wave, so that many can be added together in order to add coherently the small infarct-related, or other heart-disorder-related, signals, while noise-related signals are averaged out. As many waves as required may thus be averaged to see the disorder-related signals. For example, it has been found that approximately 100 ECG signal waves are sufficient to build up the small, fast pulses in order to detect them above the electronic and physiological noise.

More particularly, and according to one broad aspect of the present invention, there is provided a method of monitoring ECG signals, characterized in detecting a first ECG signal wave, filtering same to pass only a frequency band within a range of about 25–300 Hz, and storing the filtered signal wave in a first storage device; detecting each successive ECG signal wave, similarly filtering same to pass only a frequency band within the range of about 25–300 Hz, and storing the filtered signal wave in a second storage device; cross-correlating each of said successive signal waves, when stored in said second storage device, with the signal wave stored in said first storage device, and determining whether the maximum cross-correlation coefficient exceeds a predetermined value; averaging, with said signal waves stored in said first storage device, each of said successive signal waves having a maximum cross-correlation coefficient exceeding said predetermined value, and storing the averaged signal wave in said first storage device in place of the signal wave previously stored therein; and displaying the average signal wave stored in said first storage device.

In the preferred embodiment of the invention described below, the first ECG signal wave, and each successive ECG signal wave, is digitized and Fast-Fourier Transformed before being filtered, and inverse Fast-Fourier Transformed after being filtered and before being stored in its respective storag device.

According to other aspects of the invention, there is provided apparatus for performing the above method.

The invention thus enables the detection of very small and fast pulses in ECG signals which would otherwise not be detectable in the usual ECG monitoring equipment. Thus, the present invention has been found to enable the detection of pulses having an amplitude of less than one-fifth that of the electronic noise in the instrument, which pulses would therefore be completely masked by the noise in the usual instrument. In addition, the present invention enables the detection of very fast pulses, e.g., over 50 Hz, which would otherwise be undetected by the usual ECG equipment which cuts-out at about 50 Hz. It has been found that the HIS-bundle may be detected by using a frequency band-pass within the range of about 40–200 Hz; that small infarcts may be detected by using a frequency band-pass within the range of about 80–200 Hz; and that late potential activity may be detected by using a frequency band-pass within the range of about 25–100 Hz.

Further features and advantages of the invention will be apparent from the description below.

BRIEF DESCRIPTION OF THE DRAWINGS

The invention is herein described, by the way of example only, with reference to the accompanying drawings, wherein:

FIG. 3 illustrates the display produced by the apparatus of FIG. 1, including a first waveform (curve A) representing the detect ECG signal (idealized), and a second waveform (curve B) representing the signal after it has been processed in accordance with the method of the invention.

DESCRIPTION OF A PREFERRED EMBODIMENT

Figure 1:
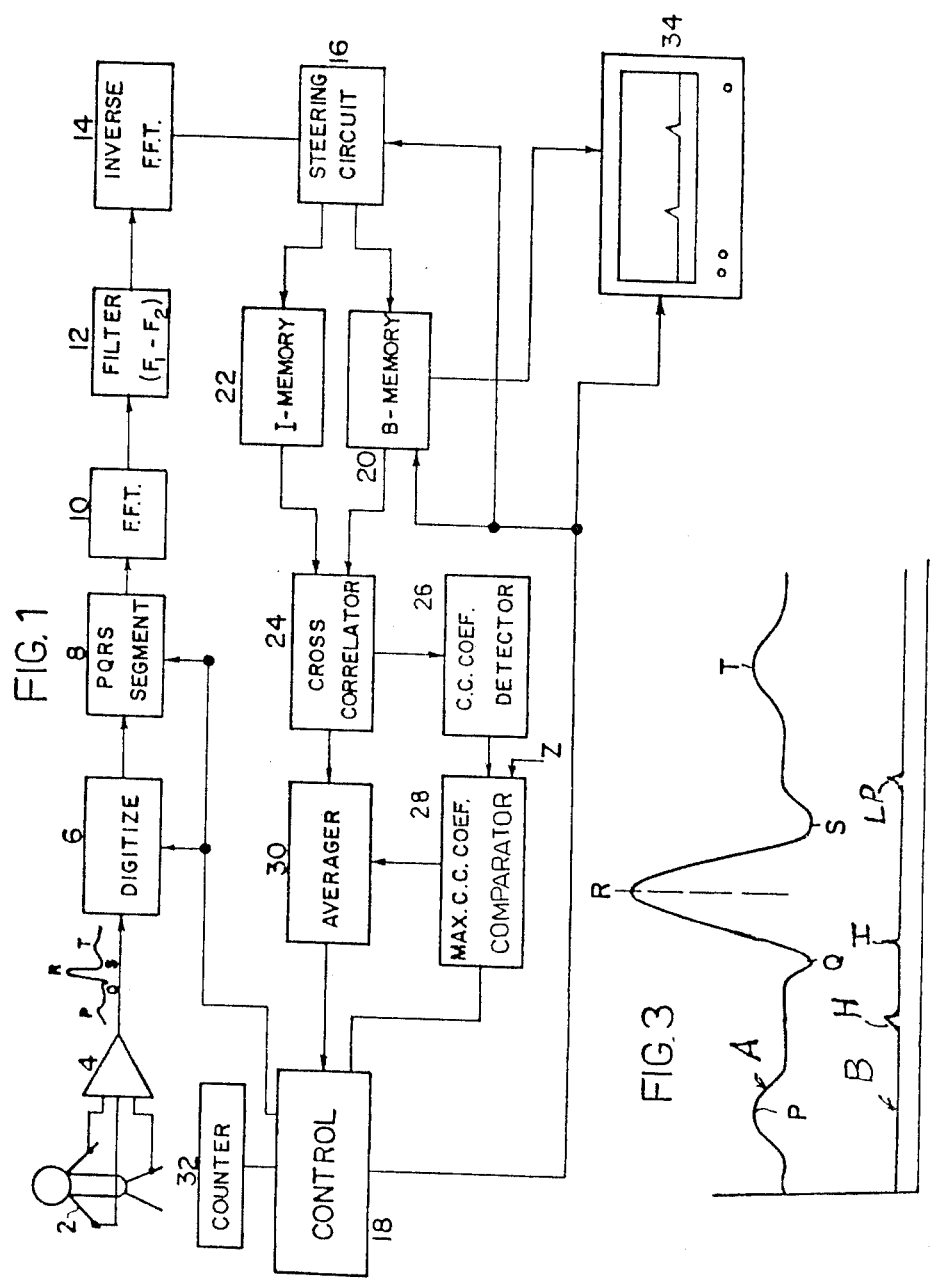
FIG. 1 is a system block diagram illustrating one form of apparatus constructed in accordance with the invention.

The apparatus illustrated in FIG. 1 or the drawings comprises the conventional skin electrodes, generally designated 2, placed in contact with the patient's skin at the usual locations to sense the electrical potentials accompanying the contraction of the heart cavities and to produce the ECG signals. The illustrated apparatus also includes the conventional amplifier 4 for amplifying the ECG signals.

The apparatus further includes a digitizer 6 which digitizes the detected ECG signals and a PQRS segmentizer 8 which extracts the data relating to the PQRS waves and arranges the data so that this segment is in the center. The digitized and segmented data is then fed to a Fast-Fourier Transform circuit (FFT) 10 which converts the digitized data from the time domain to the frequency domain, so that every periodic signal wave will show up as a peak in the output from the FFT 10.

The ECG signals are then fed from the FFT 10 to a band-pass filter 12. Filter 12 passes only a specified frequency band, which can be preset as desired, in accordance with the specific disorder to be particularly examined for, as described below. The filtered signal is then fed to an inverse FFT 14 which reconverts the filtered signal from the frequency domain back to the time domain.

The output of the inverse FFT 14 may be directed, via a steering circuit 16 as controlled by control circuit 18, either to a first storage device 20, called a B-memory, or to a second storage device 22, called an I-memory. Both memories may be 1024-bit registers for storing up to 1024 samples of the digitized and filtered ECG signals. As will be described more particularly below, the B-memory 20 is initially used for storing the first ECG signal wave, and the I-memory 22 is used for temporarily storing each successive ECG wave. The contents of the two memories are cross-correlated in a cross-correlator 24 in order to determine the similarity between the two stored waves, and also to determine the phase at which they are perfectly correlated. The cross-correlation coefficient of the two waves is determined in a detector circuit 26, and the maximum cross-correlation coefficient for each such correlated wave is compared in a comparator circuit 28 with a preselected maximum value to determine the extent of identity of the two compared cross-correlated waves. The maximum cross-correlation coefficient, represented by value "Z", may be preselected and manually inputted into comparator circuit 28. If the maximum cross-correlation coefficient exceeds this predetermined value, the signal wave stored in the I-memory 22 is averaged in an averaging circuit 30 with the signal wave stored in the B-memory 20, and the averaged signal is then stored in the B-memory 20 in place of the signal previously stored therein.

It will thus be seen that the B-memory 20 is continuously updated by each successive ECG signal wave which has been found to have a maximum cross-correlation coefficient with the previous averaged signal wave exceeding a predetermined maximum as determined by the preselected value "Z". This value would preferably be at least 80%, e.g., 90%.

After a predetermined number (e.g., about 100, or more) of successive ECG signal waves have thus been processed and averaged, as determined by a counter 32, the averaged signal wave may be displayed in display unit 34.

Figure 2:
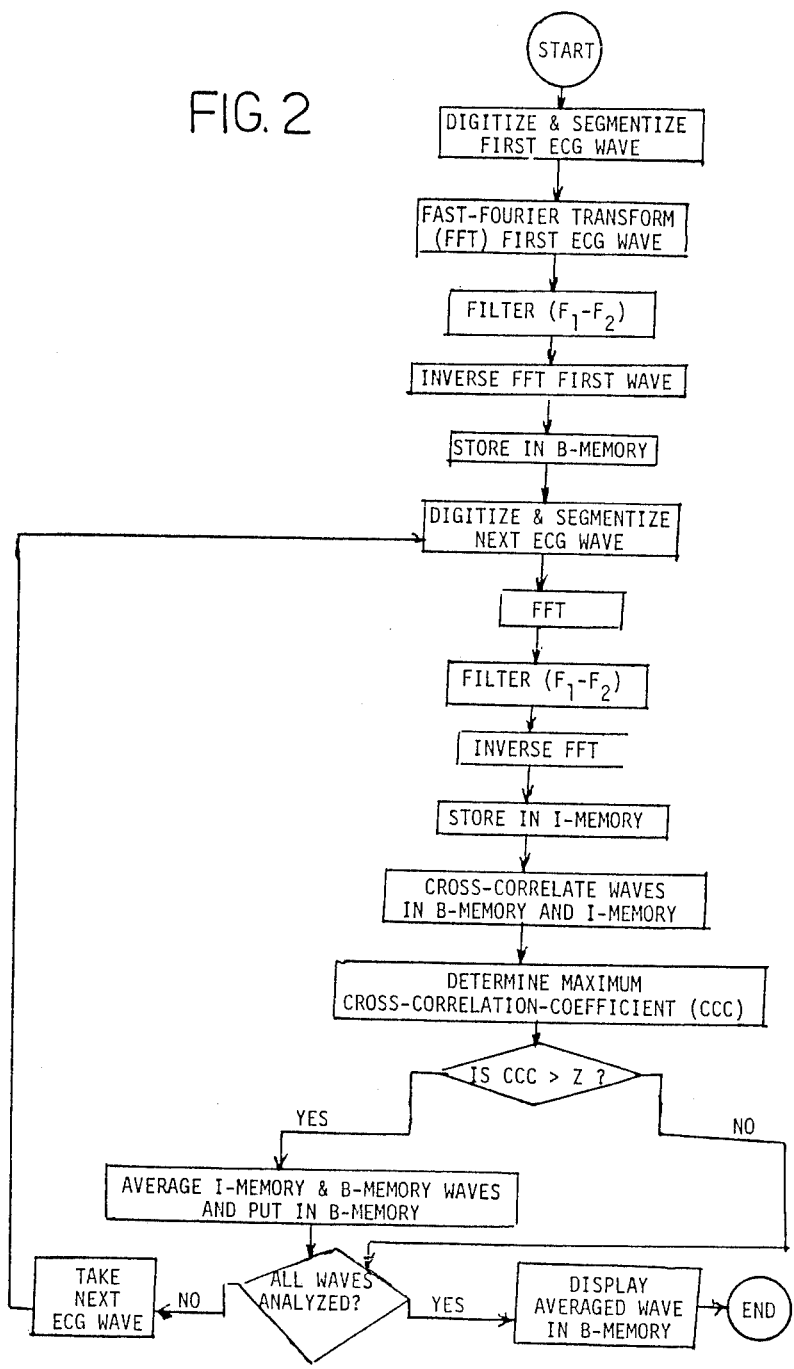
FIG. 2 is a flow chart illustrating one method of operating the apparatus of FIG. 1 in order to monitor ECG signals in accordance with the invention.

The method of monitoring ECG signals by the use of the apparatus of FIG. 1 will be better understood by reference to the flow chart of FIG. 2.

Thus, the first ECG signal wave is filtered as described above; i.e., it is digitized in digitizer 4; the PQRS segment is extracted and centered by detector 8; the digitized wave is Fast-Fourier Transformed in FFT 10 to convert it from the time domain into the frequency domain, is filtered in filter 12 to pass only the specified band-pass, and is reconverted from the frequency domain back to the time domain; and is then stored in the B-memory 20.

The next ECG wave is similarly processed and then stored in the I-memory 22. This wave in the I-memory 22 is then cross-correlated in circuit 24 with the wave in the B-memory 20, and the cross-correlation coefficient is determined in detector 26 and compared to the predetermined value "Z" in comparator 28.

If the maximum cross-correlation coefficient exceeds the predetermined value "Z" (e.g., 90%), the signal wave in the I-memory 22 is averaged with that in the B-memory 20, and the new averaged wave is then stored in the B-memory 20 in place of the previously-stored wave.

On the other hand, if the maximum cross-corrlation coefficient is found to be less than "Z", a decision is made, via counter 32, whether the preselected number of waves (e.g., 100) have been averaged; if "no", the next succeeding ECG signal wave is then processed as described above before being stored in the I-memory 22, and then cross-correlated, and its maximum cross-correlation coefficient compared with the value "Z" to determine whether or not the signal wave is to be averaged in the B-memory 20 with the previously recorded wave.

When the preselected number (e.g., 100) of waves have been averaged, the averaged wave in the B-memory is displayed in the display unit 34 (curve B) under the original ECG signal (curve A).

FIG. 3 more particularly illustrates the two signals shown in display 34, it being appreciated that the original ECG signal of Curve A is illustrated in idealized form, and that the processed signal of Curve B represents a theoretical heart condition involving several disorders.

Thus, the processed signal (curve B), includes a small fast pulse "H" between the P and Q waves; a further small, fast pulse "I" between the Q and R waves; and a still further small, fast pulse "LP" between the S and T waves. The H-pulse represents the HIS-bundle; the I-pulse represents a small infarct; and the "LP" pulse represents late-potential activity. None of these pulses would be discernable from the original ECG signal using conventional monitoring equipment because their small amplitudes would be masked by the noise, and their high frequencies would be out of the normal equipment frequency range. As will be seen in FIG. 3, the P, Q, R, S, and T waves have been removed from the displayed averaged signal (curve B), but appear in the displayed initial signal (curve A) to show the relative phases of the "H", "I" and "LP" pulses.

As indicated earlier, the frequency band-pass of filter 12 may be preselected in accordance with the specific disorder to be examined for. In general, filter 12 would provide a frequency band-pass preferably within the range of about 25–300 Hz. However, it has been found by comparing the results of this procedure with those produced by the use of a catheter to detect the ECG signal, that the HIS-bundle may be best detected by using a frequency band-pass within the range of about 40–200 Hz; that small infarcts may be best detected by using a frequency band-pass within the range of about 80–200 Hz; and that late potential activity may be best detected by using a frequency band-pass within the range of about 25–100 Hz.

While the invention has been described with respect to one preferred embodiment, it will be appreciated that many other variations, modifications and applications of the invention may be made.

What is claimed is:

1. A method of monitoring ECG signals, characterized in:

detecting a first ECG signal wave, filtering same to pass only a frequency band within a range of about 25–300 Hz, and storing the filtered signal wave in a first storage device;

detecting each successive ECG signal wave, similarly filtering same to pass only a frequency band within the range of about 25–300 Hz, and storing the filtered signal wave in a second storage device;

cross-correlating each of said successive signal waves, when stored in said second storage device, with the signal wave stored in said first storage device, and determining whether the maximum cross-correlation coefficient exceeds a predetermined value;

averaging, with said signal waves stored in said first storage device, each of said successive signal waves having a maximum cross-correlation coefficient exceeding said predetermined value, and storing the averaged signal wave in said first storage device in place of the signal wave previously stored therein;

and displaying the average signal wave stored in said first storage device.

2. The method according to claim 1, wherein only the PQRS segment of the first ECG signal wave, and each successive ECG signal wave, is detected, filtered and cross-correlated.

3. The method according to claim 1, wherein said predetermined maximum cross-correlation coefficient is at least 80%.

4. The method according to claim 1, wherein said first ECG signal wave, and each successive ECG signal wave, is digitized and Fast-Fourier Transformed before being filtered, and inverse Fast-Fourier Transformed after being filtered and before being stored in its respective storage device.

5. The method according to claim 1, wherein the detected ECG signal waves are filtered to pass a frequency band within the range of about 40–200 Hz to detect particularly the HIS-bundle.

6. The method according to claim 1, wherein the detected ECG signal waves are filtered to pass a frequency band within the range of about 80–200 Hz, to detect particularly small infarcts.

7. The method according to claim 1, wherein the detected ECG signal waves are filtered to pass a frequency band within the range of about 25–100 Hz, to detect particularly late-potential activity.

8. Apparatus for monitoring ECG signals, characterized in that it includes:

detecting means for detecting successive ECG signal waves;

filter means for filtering the detected ECG signal waves to pass a frequency band within a range of about 25–300 Hz;

first and second storage devices;

means for initially storing the first detected and filtered ECG signal wave in said first storage device, and for storing each successive filtered ECG signal wave in said second storage device;

cross-correlation means for cross-correlating each signal wave stored in said second storage device with that stored in said first storage device, and for including means determining whether the maximum cross-correlation coefficient exceeds a predetermined value;

averaging means for averaging, with the signal wave stored in said first storage device, each of said successive signal waves having a maximum cross-correlation coefficient exceeding said predetermined value, and for storing the averaged signal wave in the first storage device in place of the signal wave previously stored therein;

and display means for displaying the averaged signal wave stored in said first storage device.

9. Apparatus according to claim 8, further including a digitizer for digitizing each of said ECG signal waves before it is filtered by the filtering means.

10. Apparatus according to claim 8, further including Fast-Fourier Transform means for transforming each ECG signal wave from the time domain into the frequency domain before being filtered;

and inverse Fast-Fourier Transform means for transforming the filtered ECG signal wave from the frequency domain back to the time domain after being filtered and before being stored in its respective storage device.

11. Apparatus according to claim 8, wherein said detecting means detects only the PQRS segment of each ECG signal wave.

12. Apparatus according to claim 8, wherein said averaging means averages, with the signal wave stored in said first storage device, each of said successive signal waves having a maximum cross-correlation coefficient exceeding 80%.

13. Apparatus according to claim 8, wherein said filter means passes only a frequency band within the range of about 40–200 Hz, to detect particularly the HIS-bundle.

14. Apparatus according to claim 8, wherein said filter means passes only a frequency band within the range of about 80–200 Hz, to detect particularly small infarcts.

15. Apparatus according to claim 8, wherein said filter means passes only a frequency band within the range of about 25–100 Hz, to detect particularly late-potential activity.

* * * * *